(12) United States Patent
Wagner et al.

(10) Patent No.: US 7,805,396 B2
(45) Date of Patent: Sep. 28, 2010

(54) COMPUTERIZED IDENTIFICATION OF NORMAL AND ABNORMAL DIURNAL CORTISOL SECRETION PATTERNS AND LEVELS OF TESTOSTERONE FROM HUMAN SALIVA SAMPLES

(75) Inventors: Peter Wagner, Stockholm (SE); Lene Martin, Stockholm (SE)

(73) Assignee: Diagno-International BV, Schiphol (NL)

( * ) Notice: Subject to any disclaimer, the term of this patent is extended or adjusted under 35 U.S.C. 154(b) by 0 days.

(21) Appl. No.: 10/448,379

(22) Filed: May 30, 2003

(65) Prior Publication Data
US 2004/0039719 A1 Feb. 26, 2004

Related U.S. Application Data

(63) Continuation of application No. PCT/SE01/02670, filed on Dec. 4, 2001.

(30) Foreign Application Priority Data

Dec. 4, 2000 (SE) .................................. 0004461
Dec. 4, 2001 (SE) ..................... PCT/SE01/02670

(51) Int. Cl.
*G06F 9/44* (2006.01)
*G06F 15/18* (2006.01)
*G06N 7/02* (2006.01)
*G06N 7/06* (2006.01)
*G06G 7/00* (2006.01)

(52) U.S. Cl. ............................................ 706/52; 706/8

(58) Field of Classification Search ............. 706/8, 706/52; 600/300; 435/1.1–40.52; 424/9.1–9.81; 436/815–818
See application file for complete search history.

(56) References Cited

U.S. PATENT DOCUMENTS 5,788,640 A 8/1998 Peters

FOREIGN PATENT DOCUMENTS

| JP | 11038004 | 2/1999 |
|---|---|---|
| JP | 2000275248 | 10/2001 |
| WO | WO9904043 | 1/1999 |

OTHER PUBLICATIONS

Edward F. Krieg Jr., "An Algorithm for Detecting Features . . . ", Computers In Biology and Medicine, vol. 29, 1999, p. 229-242.

(Continued)

*Primary Examiner*—Anthony Knight
*Assistant Examiner*—Michael B. Holmes
(74) *Attorney, Agent, or Firm*—Capitol City TechLaw (57) ABSTRACT

Normal and abnormal diurnal cortisol secretion patterns are identified from human saliva samples by an in vitro method. First and second saliva samples are taken from one human individual at first and second predetermined times during the same day. A first cortisol concentration is determined in the first saliva sample, and a second cortisol concentration is determined in the second saliva sample. An abnormal secretion pattern is then compared to a normal secretion pattern with the help of a fuzzy logic algorithm. A function of the hypothalamic-pituitary-adrenal (HPA) axis is then determined for the human individual. Optionally, a testosterone level is determined from one of the samples and is used in combination with the cortisol concentrations to provide a redefined determination.

17 Claims, 7 Drawing Sheets

OTHER PUBLICATIONS

Raff Hershel, "Late-night Salivary Cortisol . . . ", BIOSIS, PREV199800431798, vol. 83, No. 8, p. 2681-2686, Journal Of Clinical Endo.

Arita S., "Quantitative Analysis of Glucose Tolerance Testing . . . ", Nippon Rinsho, vol. 54, No. 10, Oct. 1996, p. 2807-2811.

Roland Rosmond, "Stress Related Cortisol Secretion in Men . . . ", Journal of Clinical Endocrinology and Metabolism, vol. 83, No. 6, p. 1853-1859.

Normal HPA axis function

*Fig 2b*

Activated HPA axis function

*Fig 2c*

Blunted HPA axis function

Inverted HPA axis function

COMPUTERIZED IDENTIFICATION OF NORMAL AND ABNORMAL DIURNAL CORTISOL SECRETION PATTERNS AND LEVELS OF TESTOSTERONE FROM HUMAN SALIVA SAMPLES

CROSS REFERENCE TO RELATED APPLICATION

This application is a continuation application of International Application No. PCT/SE01/02670, which was filed Dec. 4, 2001, and which was published in English.

TECHNICAL FIELD

The present invention relates to identification of normal and abnormal diurnal cortisol secretion patterns and levels of testosterone from human saliva samples, so as to determine the function of the hypothalamic-pituitary-adrenal (HPA) axis in individual subjects.

BACKGROUND ART

Figure 1:
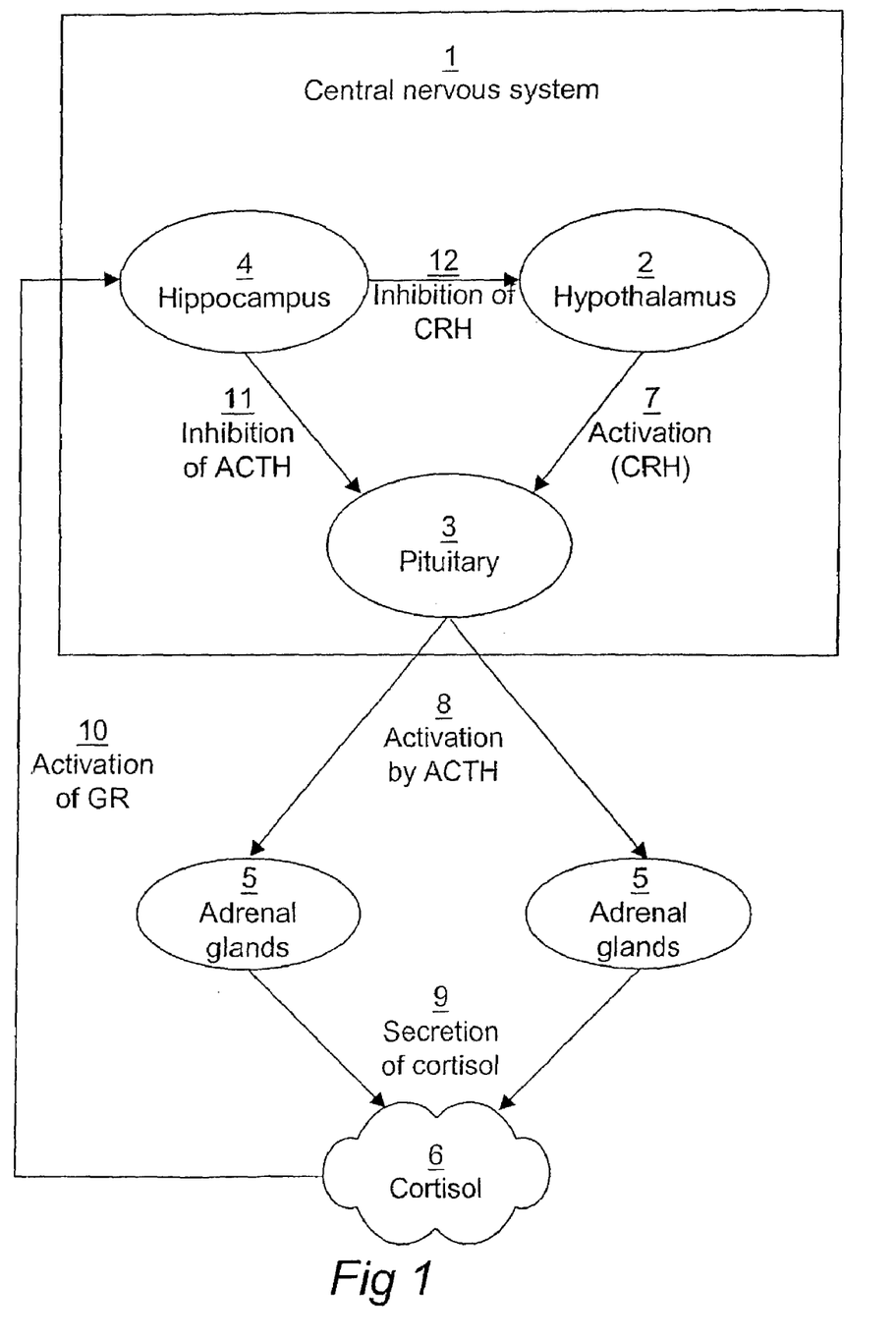
FIG. 1 is a schematic illustration of the hypothalamic-pituitary-adrenal (HPA) axis.

The hypothalamus is a small, central part of the brain with several important regulatory functions, for example as regards physiologic response to external stress, body weight (especially the metabolically unfavorable abdominal obesity), the sleep-wake cycle and mood fluctuations. As shown in FIG. 1, the hypothalamus 2 is connected to the pituitary 3 as part of the central nervous system 1 and controls the secretion of different hormones from this endocrine gland. One of these hormones is ACTH (adenocorticotropic hormone), the secretion of which is activated through secretion of corticotropin releasing hormone (CRH) from the hypothalamus 2, as indicated by reference numeral 7 in FIG. 1. In response, this will activate secretion of the stress-related hormone cortisol 6 from the cortex of the adrenal glands 5 (see reference numerals 8 and 9 in FIG. 1).

Cortisol 6 circulates in the bloodstream and activates specific receptors, such as the glucocorticoid receptor (GR), in another small part of the brain, the hippocampus 4. This activation is indicated as 10 in FIG. 1 and leads to inhibition of the release of ACTH (reference numeral 11) as well as CRH (reference numeral 12). Thus a feedback loop is established, which regulates the blood concentration of cortisol.

The joint operation of the above functions, in the medical literature commonly referred to as the hypothalamic-pituitary-adrenal (HPA) axis, constitutes an important mechanism for maintaining steady state in the human organism. Disturbances in this mechanism have been shown to lead to metabolic complications, such as increased insulin resistance and abdominal obesity. These metabolic abnormalities are associated with increased risk for cardiovascular disease, the major cause of death in industrialized countries. A review of the above is found in "Neuroendocrine perturbations as a cause of insulin resistance" in Diabetes/Metabolism Research and Reviews 1999; 15:427–441, by Björntorp P. For a more detailed description see "Psychoneuroendocrine aspects on the metabolic syndrome", ISBN 91-628-3195-X, by Rosmond R., Göteborg University 1998.

Abnormal concentrations of cortisol have also been shown to be the biochemical mechanism for the influence of external stress factors on the metabolic system, which lead to increased risk for heart disease, in both humans and experimental animals.

Since the concentration of this hormone in blood serum shows diurnal variation, the functional analysis of the HPA axis requires a number of cortisol measurements during the day, usually seven to ten, and may also have to be complemented by further examinations.

The saliva level of cortisol is strongly correlated to the level in blood serum, as reported by Aardal E. and Holm AC. in "Cortisol in saliva—reference ranges and relation to cortisol in serum" in European Journal of Clinical Chemistry and Biochemistry 1995:33(12):927–32. Test equipment for measuring the amount of saliva cortisol, using Radio Immune Assays (RIA), are commercially available from Orion Diagnostica, Espoo, Finland and have been used to characterize the HPA axis in a population based study. However, the identification of abnormalities has up to now only been possible by means of statistical analysis of groups of subjects. Due to the large inter- and intra-individual variability, it has hitherto not been possible to classify individual subjects.

Testosterone is the male sexual hormone but is present also in females, albeit in a very low concentration. This hormone interacts with cortisol in a fairly complex way, as described by Björntorp P. in "Hypothalamic origin of prevalent human disease" in "Hormones, Brain and Behaviour", Academic Press, 2001 (in press), which can be summarized as follows:

1. In males low testosterone implies a more negative response to cortisol alteration, compared to the average or intermediate testosterone level. However, a high testosterone level also implies negative effects. Therefore, three levels of testosterone have to be defined, i.e. low, normal/intermediate and high. In males the gonads, i.e. the testicles, secrete most of the testosterone.

2. In females testosterone levels are normally low, i.e. testosterone may be close to zero without identifiable negative effects. However, testosterone levels in the upper quartile in a normal population are associated with increased risk for cardiovascular disease, and this relationship is stronger when cortisol levels are abnormal. It is assumed that the testosterone in females is secreted by the adrenal cortex, as is cortisol.

In a recent study by Shifren J L, Braunstein G D, Simon J A, et al., "Transdermal testosterone treatment in women with impaired sexual function after oophorectomy", N Engl J Med (United States), September 2000, 343(10) p 682–8, it was found that a certain (very low) level of testosterone may be necessary also for women, in order to maintain general well-being and a satisfying sex life.

Testosterone can be measured in saliva, using the same principle as when measuring cortisol, as reported by Obminski Z and Stupnicki R in "Comparison of the testosterone-to-cortisol ratio values obtained from hormonal assays in saliva and serum" in J Sports Med Phys Fitness 1997 March; 37(1): 50–55, by Navarro M A et al. In "Salivary testosterone in postmenopausal women with rheumatoid arthritis", J Rheumatol 1998 June; 25(6):1059–62 and by Granger D A et al in "Salivary testosterone determination in studies of child health and development" in Horm Behav 1999 February; 35(1): 18–27.

SUMMARY OF THE INVENTION

In view of the above shortcomings in the prior art, the present invention seeks to provide a method of identifying normal and abnormal diurnal cortisol secretion patterns from human saliva samples, specifically so that the function of the HPA axis may be determined for individual subjects in a convenient and completely structured manner with high accuracy.

The objective is achieved through a computerized method of identifying normal and abnormal diurnal cortisol secretion patterns according to the attached independent patent claims.

According to a preferred embodiment, only two measurements of saliva cortisol, compared to seven to ten measurements in the prior art, are performed during the same day at predetermined times. The two measurement values of saliva cortisol are input to a computer program, which will interpret the values by means of a fuzzy logic algorithm. The main output of the computer program is one of three possible classifications of the HPA axis function, i.e. normal, activated or blunted. The last two of these three classifications correspond to different levels of metabolic abnormalities and can be used by the tested individual as a basis for corrective measures or by physicians as a basis for therapeutic interventions.

Advantageously, the first saliva sample is used also for determination of the testosterone level, which is analyzed in a similar manner.

The use of the computer program according to the invention will not only for the first time allow determination of the function of the HPA axis for individual subjects rather than for an entire population; it will, moreover, provide considerable convenience, since only two saliva cortisol measurements are required for the determination of the diurnal cortisol pattern. In addition, the level of testosterone, which influences the evaluation of the HPA axis, can be measured simultaneously, wherein the computer program will use the measured testosterone value to further refine the evaluation of the HPA axis.

The invention also guarantees a structured approach, since the HPA axis function will be determined in exactly the same way in every examination. Furthermore, the computer program quantifies the degree of membership in the particular classification group by means of a group membership index, which will allow an even more detailed analysis of the function of the HPA axis, as will be described in more detail in the following.

Other objects, features and advantages of the present invention will appear from the following detailed disclosure, from the appended drawings as well as from the subclaims.

BRIEF DESCRIPTION OF THE DRAWINGS

A preferred embodiment and various other aspects of the present invention will now be described in more detail, reference being made to the accompanying drawings, in which.

DETAILED DISCLOSURE OF THE INVENTION

As will be described in detail in the following, the main features of the invention involve:

1. The use of only two measurements of saliva cortisol concentration, sampled at defined times the same day.

2. A cortisol analysis algorithm, preferably implemented as a computer program, which analyses the measurement values and evaluates if the HPA axis function is normal or abnormal. If the HPA axis is abnormal, the program may also determine the type of abnormality.

3. Use of the above-mentioned computer program for remote distribution of tests and test results over the Internet.

Preferably, the invention also involves a testosterone evaluation algorithm, advantageously implemented as part of the computer program, which evaluates the level of testosterone and integrates this information in the final determination of HPA axis abnormality.

As stated above, the invention will make it possible to use saliva cortisol measurements, and optionally testosterone measurements, as a diagnostic tool in health care and for prevention of disease in the general population. Use of the Internet makes the test available to a large number of individuals.

Figure 2A:
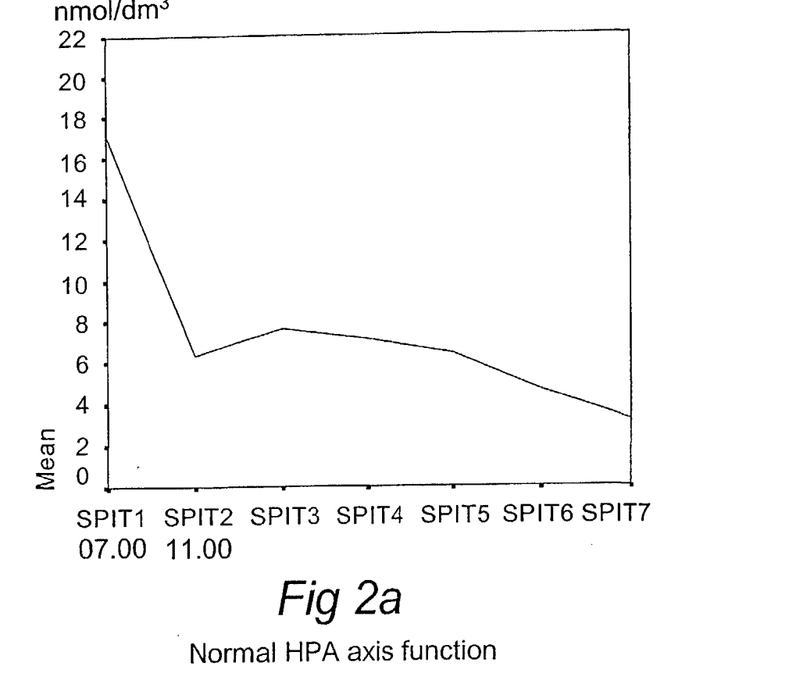
FIGS. 2a–2c are graphical representations of diurnal cortisol variation according to three different main categories of HPA axis function.
Figure 2B:
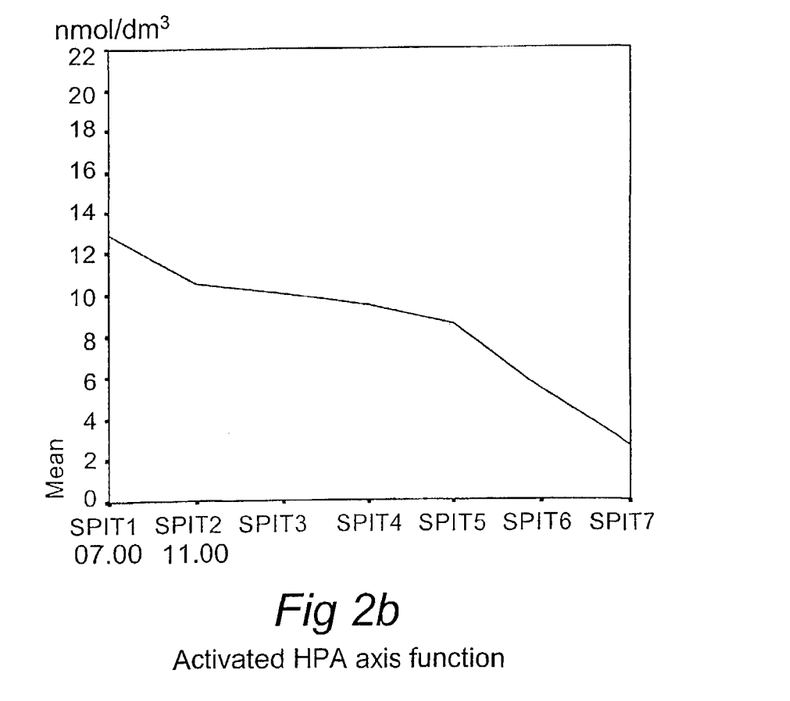
Figure 2C:
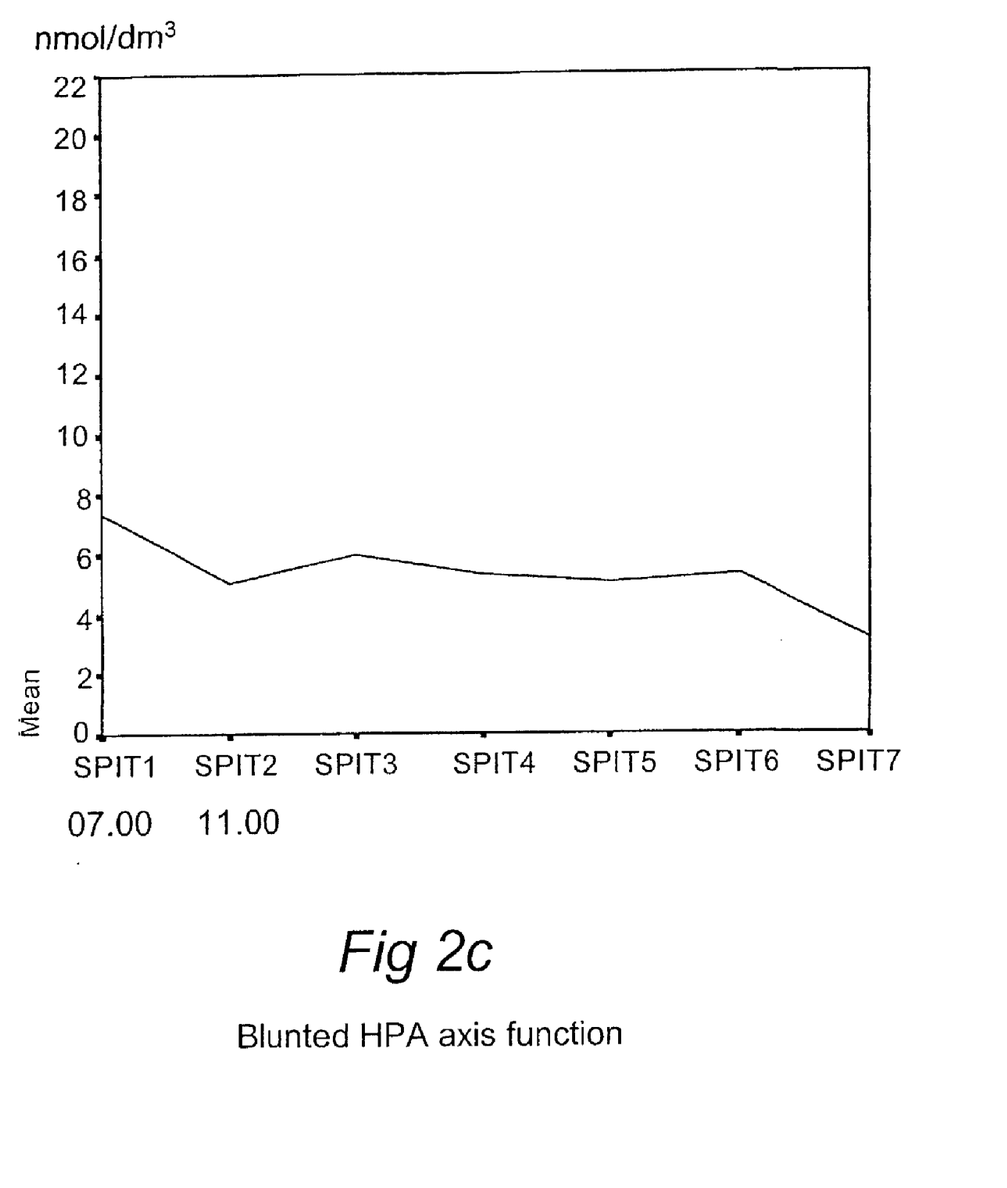

FIGS. 2a–2c illustrate typical diurnal variations in saliva cortisol concentration according to the three different main categories of HPA axis function, i.e. normal, activated and blunted, respectively. The graphs illustrate typical concentration values, in $nmol/dm^3$ (y axis), during seven different times of the day (denoted spit1 ... spit7 on the x axis). Conventionally, as mentioned above, saliva cortisol concentration is measured at (at least) all these seven moments through the day. According to the invention, on the other hand, saliva cortisol concentration is only measured at the first and second of these different times of the day, i.e. at spit1 and spit2. Preferably, the two measurements are made at 07.00 am and 11.00 am, as shown in FIGS. 2a–2c.

Figure 3:
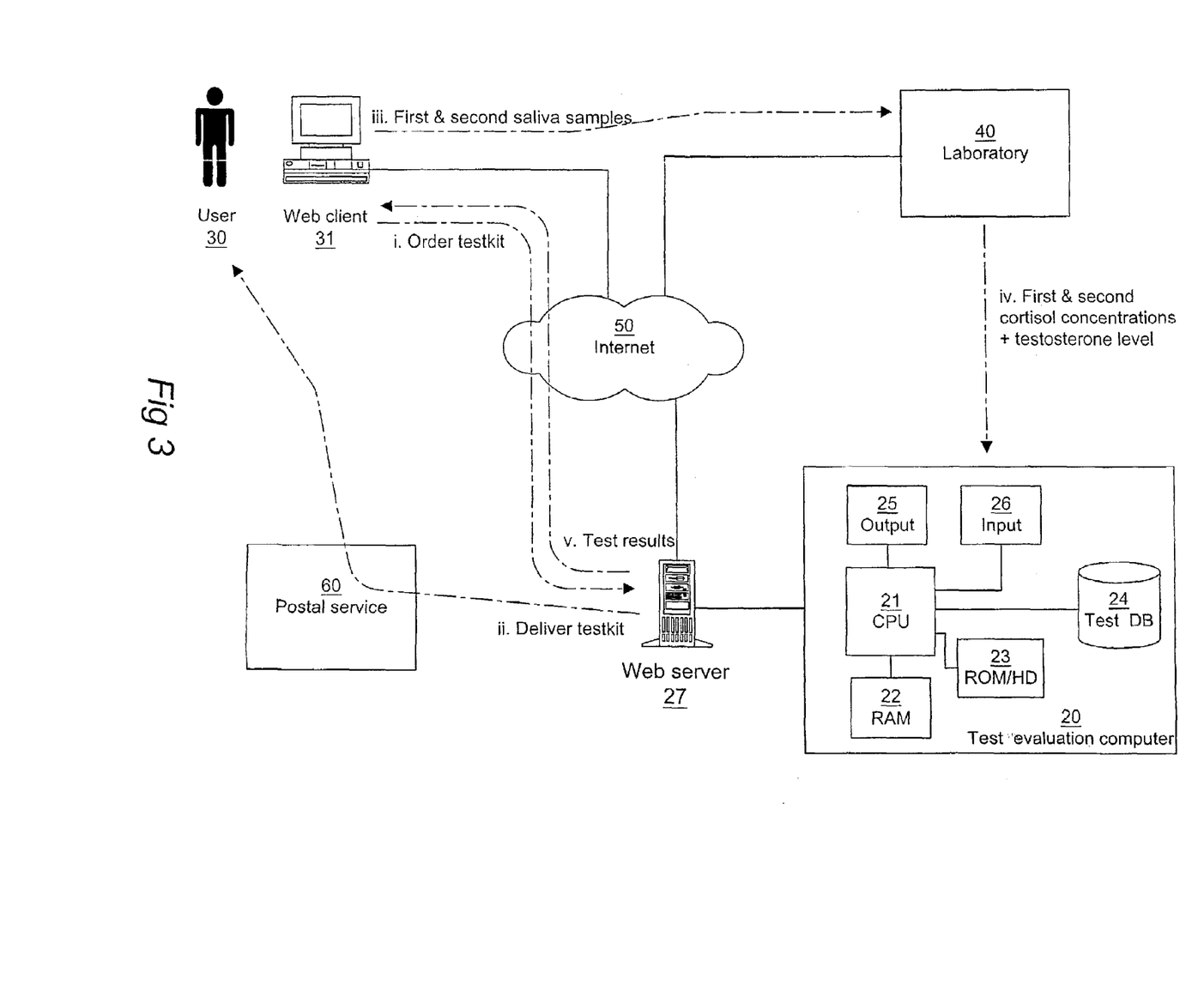
FIG. 3 is a schematic overview of a computer system environment in which the computer program according to the invention may be executed, when used in an Internet application.
Figure 4:
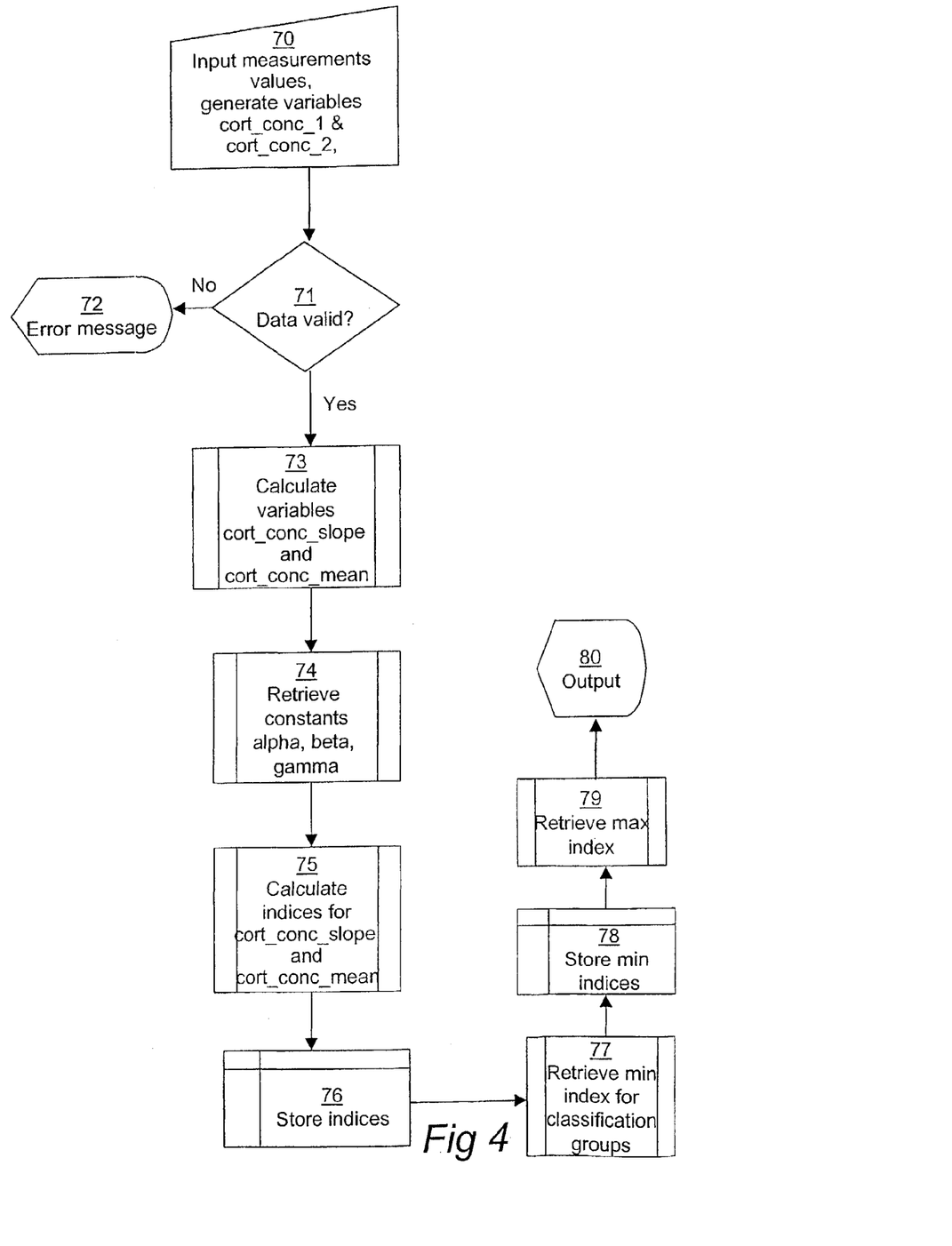
FIG. 4 is a flowchart of the main steps of the method according to a preferred embodiment.

The test procedure will now be described with reference to FIGS. 3 and 4. FIG. 3 illustrate a test evaluation computer 20 having a central processing unit (CPU) 21, a work memory 22 such as a random access memory (RAM), and a permanent memory 23 such as a read-only memory (ROM) and/or a hard disk (HD). The test evaluation computer 20 has operative access to a database (DB) 24 for storing test results for a plurality of individuals, as will be described later with reference to an Internet use case. The database 24 may be stored locally in the test evaluation computer 20 (for instance in a portion of the permanent memory 23), but it may equally well be located externally to the computer 20. In the latter case, the computer 20 will preferably gain access to the database 24 through local connection (serial or parallel interface, infrared interface, accessory bus, etc.) or through a networked connection to a local area network (LAN) or a wide area network (WAN), such as the Internet 50.

Additionally, the computer 20 has input means 26 as well as output means 25. The input means 26 may comprise various different devices generally known per se, such as a keyboard, a mouse, or any type of digital data input interface (modem, ISDN, TCP/IP-based information exchange, etc). Correspondingly, the output means 25 may comprise various different known devices, such as a CRT display or an LCD display, a printer, or any type of digital data output interface (modem, ISDN, TCP/IP-based information exchange, etc). Generally, all hardware components of the test evaluation computer 20 may be implemented by commercially available components, as is readily realized by a man skilled in the art. Moreover, the test evaluation computer 20 is provided with a commercially available operating system, such as the Microsoft Windows family (e.g. NT), Unix (e.g. Linux), etc.

Next, with particular reference to FIG. 4 a presently preferred embodiment of the test procedure will be described, where the test evaluation computer 20 is used as a stand-alone computer. Another embodiment, where the test evaluation computer 20 is used in an Internet application, will follow later.

Test Procedure

1. Saliva from the tested subject is obtained at 07.00 and 11.00, as indicated in FIGS. 2a–2c, using conventional technique.

2. The cortisol concentrations in the two test samples are measured in a conventional analysis machine, for instance one based on the above-mentioned RIA technique.

3. The testosterone level is determined for one of the saliva samples, preferably the first sample (07.00), using the same basic principle (for instance RIA technique) as when determining the cortisol concentrations.

4. The first and second measurement values are entered into the working memory 22 of the computer 20 through its input means 26 (step 70 in FIG. 4). This may be performed either automatically using electronic communication between the analysis machine and the computer, or manually by the laboratory personnel using e.g. a keyboard and/or a mouse. Alternatively, particularly in an Internet application, the measurement values may be read from the test database 24.

5. The permanent memory 23 is provided with a computer program comprising program code adapted to be read into the working memory 22 and executed by the processor 21 so as to perform the following test evaluation algorithm in an ordered sequence of operations and calculations:

First, in step 70, two measurement variables, cort_conc_1 and cort_conc_2, are formed from the first and second measurement values, respectively.

Then, in a step 71 the variables cort_conc_1 and cort_conc_2 are validated so as to eliminate obviously unrealistic values. If necessary, an error message is presented in a step 72, wherein the execution will terminate.

Otherwise, in a step 73 the program calculates two analysis variables, namely cort_conc_slope, which is the difference between the first and second measurement variables (cort_conc_1 and cort_conc_2), and cort_conc_mean, which is the arithmetic mean of the variables cort_conc_1 and cort_conc_2.

A set of three constants, alpha, beta and gamma, is predefined in the program for each of the two analysis variables, i.e. cort_conc_slope and cort_conc_mean. These constants are retrieved in a step 74.

Two indices, which are decimal numbers between 0.00 and 1.00, are calculated in a step 75 for each variable. The first index, high_ind, defines to which degree the value of the variable can be regarded as high. The second index, low_ind, similarly defines to which degree the value of the variable can be regard as low. Preferably, it is calculated as the complement of high_ind (i.e., low_ind=1−high_ind). These index calculations are based on the three above-mentioned constants, alpha, beta and gamma, for each indexed variable. The values of these constants have been empirically derived before execution of the program. In one implementation made by the inventors the constants are based on a survey of the scientific literature combined with information from a study population, consisting of 550 randomly selected middle-aged Swedes. The constants are based on statistical correlations between the measurement values and the different types of HPA axis function. Correlations with metabolic and physiologic risk factors for heart disease were used to define the abnormalities of the HPA axis.

The constants, alpha, beta and gamma, are used in the following way in step 75 when calculating the first index, high_ind, for each of the variables:

If the variable's value is lower than (or equal to) constant alpha, the index is set to 0.00.

If the variable's is larger than (or equal to) constant gamma, the index is set to 1.00.

If the variable's value is larger than constant alpha and smaller than (or equal to) constant beta, a program function calculates an index between 0.00 and 0.50. More specifically, the index is set to $2*(((x-alpha)/(gamma-alpha))2)$, where x is the value of the variable.

If the variable's value is larger than (or equal to) constant beta and smaller than constant gamma, a program function calculates an index between 0.50 and 1.00. More specifically, the index is set to $1-(2*(((x-gamma)/(x-alpha))2))$, where x is the value of the variable.

The calculated indices are stored in a step 76.

Each possible HPA axis is characterized by a particular combination of the calculated two indices. These combinations are defined in a basic group definition matrix:

| Group | Cort_conc_slope | Cort_conc_mean | Conclusion |
|-------|-----------------|----------------|------------|
| A | High | High | Normal HPA axis |
| B | High | Low | Normal HPA axis |
| C | Low | High | Activated HPA axis |
| D | Low | Low | Blunted HPA axis |

This matrix has four possible categories, labeled A–D. Categories A and B=normal HPA axis, category C=activated HPA axis, and category D=blunted HPA axis. The calculated indices from the tested individual are used to assign the individual to a particular classification group in the following way:

A membership index is calculated for each classification group, as defined in the above table, by retrieving the lowest index value in the corresponding column of the group definition matrix, as shown in a step 77. Thus, for each group (A–D) the membership index is defined as min(index_for_cort_conc_slope, index_for_cort_conc_mean). This minimum value is stored in a step 78.

Then, the tested subject is assigned to the group with the highest membership index in a step 79.

The above may be exemplified as follows:

EXAMPLE

In a normal subject, the value of cort_conc_slope should be high and the value of cort_conc_mean may be either high or low. This appears from the leftmost portion of the graph in FIG. 2a.

The corresponding indices for a subject could then be as follows:

The high_index for cort_conc_slope might be 1.00 (corresponds to a high test value in the morning sample at 07.00 am and a low test value in the second sample at 11.00).

The high_ind for cort_conc_mean might be 0.6.

This subject belongs to the group with normal HPA axis (group A in the group definition matrix) with a membership value of 0.6 (i.e. the minimum of 1.00 and 0.6). The membership value of any other group would be less than this value.

* * *

Borderline cases, i.e. two classification groups with identical membership indices, may occur. These subjects are labeled as borderline normal/activated, borderline normal/blunted or borderline activated/blunted as appropriate with regard to the indices.

In a step 80, once the program has been able to either determine a single classification group for the subject, or a borderline case as described above, the result is output through the output means 25.

The evaluation is refined by the addition of the information about testosterone level. The testosterone value is evaluated as follows:

1. In males: If the value is below a threshold value, the level is labeled as low. If the value is above this threshold value, the level is labeled normal.

2. In females: If the testosterone value is above a threshold value it is labeled high, otherwise it is labeled normal.

Figure 6:
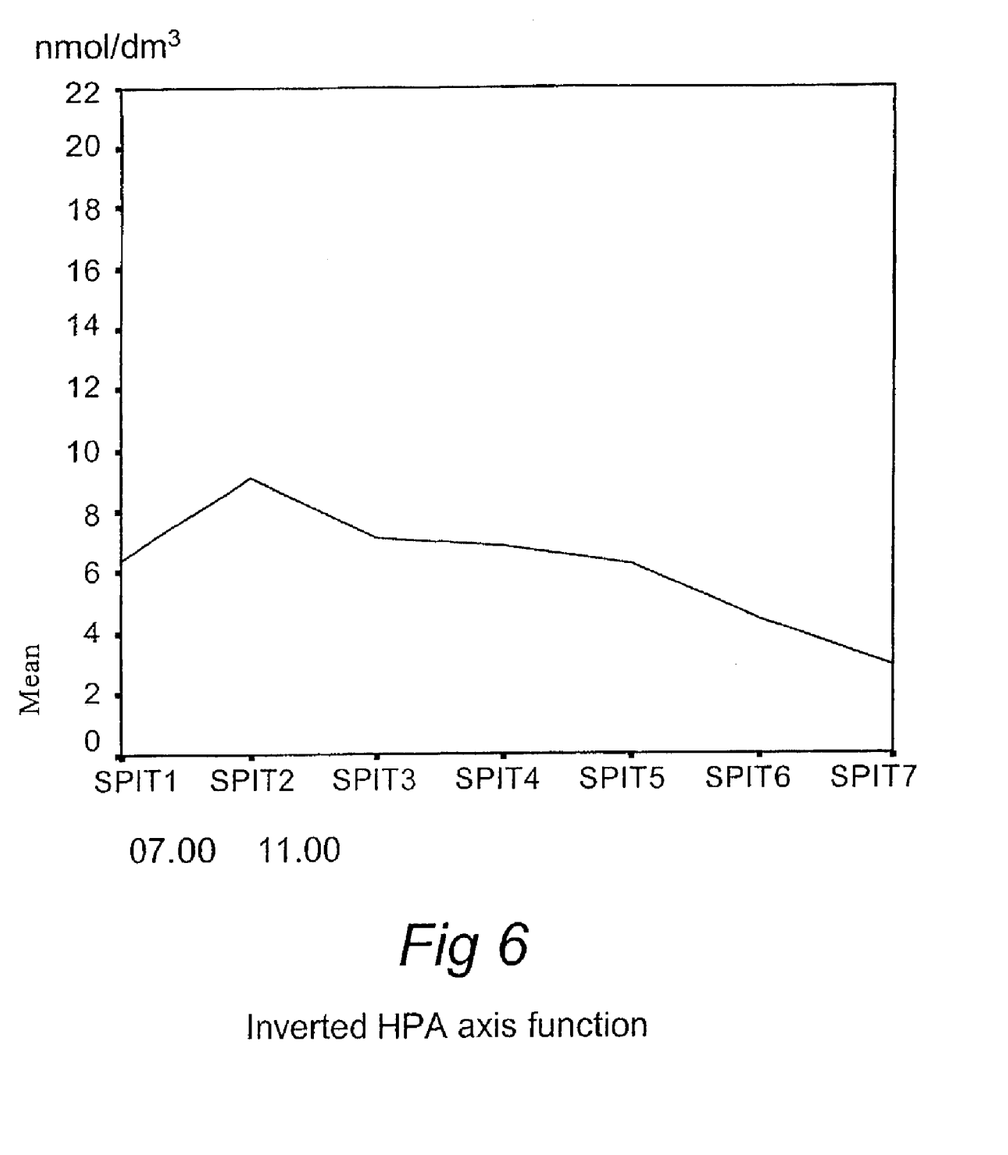
FIG. 6 is a graphical representation of a diurnal cortisol variation known as inverted HPA axis function.

Advantageously, the program is adapted to evaluate whether the second cortisol concentration (cort_conc_2) is higher than the first cortisol concentration (cort_conc_1). Such a situation will be labeled as inverted HPA axis and is illustrated in FIG. 6. This abnormality is associated with disturbed sleep pattern and/or diurnal rhythm.

Internet Use

The procedure described above may preferably be used over the Internet, as will be explained with reference to FIGS. 3 and 5.

1. The customer (user 30) uses a web client 31 to access a web site on a web server 27, which presents relevant information.

2. The customer orders a test kit (see dot and dash line i in FIG. 3) and pays using a standard electronic payment procedure, which is not described further herein.

3. The customer receives a test kit to his/her address, using standard postal delivery 60 (see line ii in FIG. 3). This test kit contains an ID code, which is unique for each test kit.

4. The customer sends the test kit, which now contains the first and second saliva samples, to a contracted laboratory 40, using a preaddressed envelope, delivered to the customer together with the test kit. See line iii in FIG. 3.

5. The laboratory performs the analyses and reports the results together with the test ID to the test database 24, which is connected to the web server 27 and the test computer 20. See line iv in FIG. 3.

6. The customer accesses the web site a second time and enters the test kit ID code. The program described above retrieves the test results from the database by means of the ID code, performs the evaluation as described above and presents the conclusion to the customer, who has the option to obtain a print-out if he/she so wishes. See line v in FIG. 3. Preferably, the conclusion involves not only the results from the measurement evaluation (i.e. the determined category of HPA axis functionality) but also a prediction of the risk of deranged health for the customer.

Figure 5:
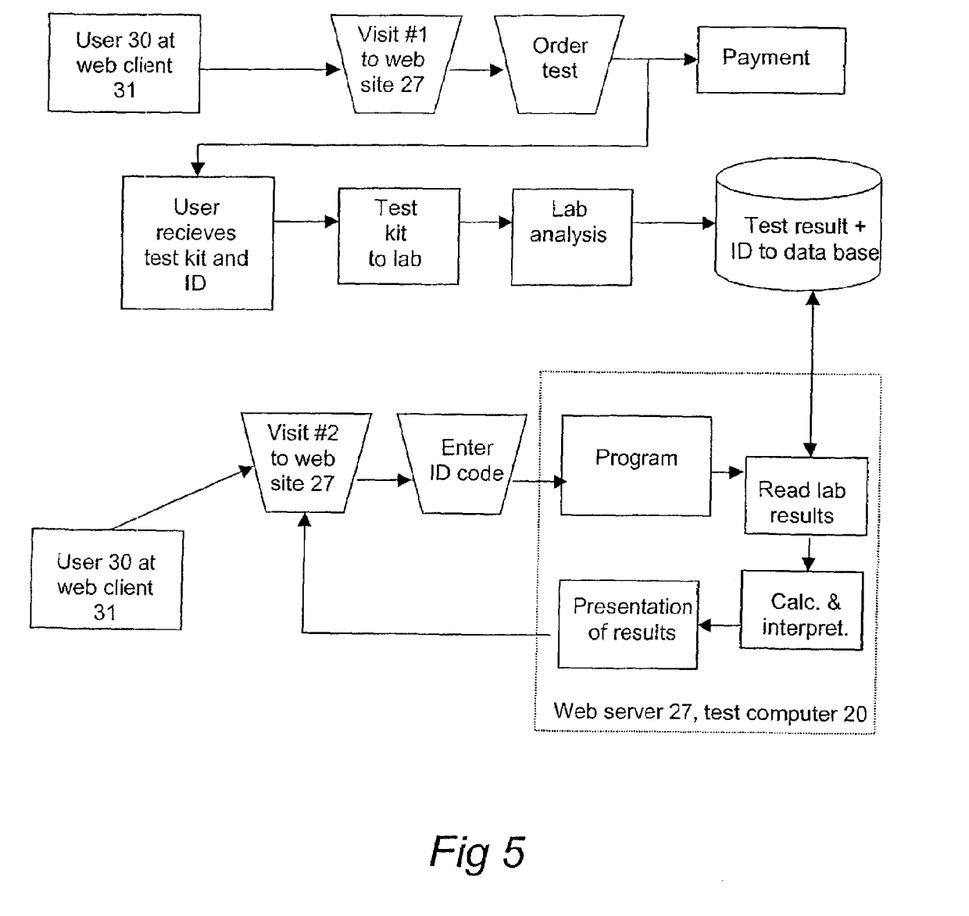
FIG. 5 is a flowchart of an Internet use case for remote test and evaluation of diurnal cortisol secretion patterns from human saliva samples.

The flow is depicted in FIG. 5 and may be carried out for cortisol concentration measurements only, for both cortisol concentration measurements and a testosterone measurement, or for a testosterone measurement alone. At present, however, a combination of cortisol concentration measurements and a testosterone measurement is believed to provide the highest accuracy in the analysis of the HPA axis function and the prediction of the risk of deranged health for the customer.

Program Implementation

An embodiment of the described program is implemented using the syntax module in Statistical Package for Social Sciences (SPSS) and also using VBScript for use over the Internet. The program can, however, be implemented in any other general purpose programming or scripting language, including but not limited to C++, Java, Visual Basic, Delphi or JavaScript.

Program Validation

Program output has been compared to actual measurement values (seven each day) from the study population mentioned above. The program clearly identified the three main types of HPA axis diurnal pattern, see FIGS. 2a–2c, using only two of the saliva cortisol measurements (at 07.00 am and 11.00 am).

The classifications (in three main categories) have been compared to the outcomes of associated tests regarding saliva cortisol. These tests are:

1. Response to a standardized lunch. Food induces an increase in blood and saliva cortisol. This increase can be measured by repeated tests and used as an aid in the determination of the function of the HPA axis in a particular individual.

2. Dexamethason suppression test. Dexamethason is a synthetic substance, essentially identical with the cortisol, secreted from the adrenal glands. When dexamethason is administered in the form of pills, the blood and saliva cortisol is decreased. The rate of decrease can be measured by repeated tests and used as an aid in the determination of the function of the HPA axis in a particular individual.

The correlations between the results from these two associated tests and the classification performed by the computer program were very good, indicating that the same information was established using the program's analysis of only two tests compared to the conventional method, using statistical analysis of seven tests.

The classifications (in three main categories) were also compared to known risk factors for heart disease and significant associations were observed. One example is insulin resistance (s-insulin/s-glucose quotient) in males, which was higher in the groups with abnormal HPA axis. Hence, the method apparently identifies individuals with rather discrete deviations from normality.

The evaluation is further refined by the addition of the information about testosterone levels. This results in a doubling of the number of groups, since the testosterone value may be either normal or abnormal, i.e. abnormal when high in women or low in men, and otherwise normal.

Advantages

The invention allows determination of the functional state of the HPA axis, based on only two measurements of the concentration of cortisol in saliva, performed the same day at defined times, optionally in addition to one simultaneously performed measurement of testosterone level in saliva. A computer program performs the interpretation of the test results. The invention facilitates practical use of measurements of saliva cortisol for determination of the function of the HPA axis, since only two saliva tests are needed from each subject. The use of a computer program for evaluation of the measurement values guarantees that all subjects are evaluated in an identical way in all examinations. The derangements in HPA axis function, identified by the program, are relevant for the health of individual subjects, and the computer-based analysis of the measurement values gives new information, hitherto not available. Use over the Internet provides access to the system to a large number of individuals. The addition of testosterone values improves the relationship between the diagnostic groups and risk factors for e.g. cardiovascular disease.

The present invention has been described above with reference to a preferred embodiment. However, other embodiments than the one disclosed above are equally possible within the scope of the invention, as defined by the attached independent patent claims.

The invention claimed is:

1. An in vitro method of identifying normal and abnormal diurnal cortisol secretion patterns from human saliva samples, wherein first and second saliva samples are taken from one human individual at first and second predefined times during a day, a first cortisol concentration is determined in the first saliva sample, and a second cortisol concentration is determined in the second saliva sample, comprising the steps of:
  providing first and second variables;
  assigning values to the first and second variables which are associated with the determined first and second cortisol concentrations;
  providing a set of predefined constants for each variable;
  calculating, for each variable, a first fuzzy logic index to represent a degree to which the variable has a high value in relation to the predefined constants;
  calculating, for each variable, a second fuzzy logic index to represent a degree to which the variable has a low value in relation to the predefined constants;
  matching different combinations of the first and second fuzzy logic indices, as calculated for the first and second variables, with predetermined definitions of a normal diurnal cortisol secretion pattern and at least one abnormal diurnal cortisol secretion pattern; and
  selecting the definition where the best correspondence occurs.

2. The method according to claim 1, wherein the first variable is calculated as a difference between the determined first and second cortisol concentrations, and wherein the second variable is calculated as an arithmetic mean of the determined first and second cortisol concentrations.

3. The method according to claim 1, wherein the first and second fuzzy logic indices are decimal values between 0.0 and 1.0.

4. The method according to claim 1, wherein the set of predefined constants comprises three constants and wherein the first fuzzy logic index for each of the first and second variables is set to:
  0.0, if the variable is smaller than or equal to a first constant in the set of predefined constants;
  1.0, if the variable is larger than or equal to a third constant in the set of predefined constants;
  a value between 0.0 and 0.5, if the variable is larger than the first constant in the set of predefined constants;
  a value between 0.5 and 1.0, if the variable is larger than the second constant and smaller than the third constant.

5. The method according to claim 1, wherein the second fuzzy logic index is calculated as the complement of the first fuzzy logic index.

6. The method according to claim 1, further comprising the step of:
  determining a function of the hypothalamic-pituitary-adrenal (HPA) axis for said human individual in response to the selected diurnal cortisol secretion pattern definition, said function being one of the following: normal HPA axis function; activated HPA axis function; and blunted HPA axis function.

7. The method according to claim 6, further comprising the steps of:
  evaluating a level of testosterone in at least one of said first and second saliva samples, and
  using the result of the testosterone evaluation when determining the function of the HPA axis.

8. The method according to claim 1, further comprising the step of:
  predicting a risk of deranged health for said human individual based on the selected diurnal cortisol secretion pattern definition.

9. The method according to claim 1, wherein the difference between the first and second predefined times during the day is 4 hours.

10. The method according to claim 9, wherein said first predefined time is at 07:00 am and said second predefined time is at 11:00 am during the same day.

11. A computer program product directly loadable into an internal memory of a computer, comprising program code for performing the steps of claim 1 when executed on said computer.

12. A computer program product as defined in claim 9, embodied on a computer-readable medium.

13. A computer having a memory and a processor, the memory containing program code for performing the steps of claim 1 when executed by said processor.

14. A method for remote test and evaluation of diurnal cortisol secretion patterns from human saliva samples, comprising the steps of:
  providing a server computer, from which a user may order a diurnal cortisol secretion saliva test using a client computer;
  in response to receiving an order from the user, dispatching a test kit to the user, said test kit being adapted to receive first and second samples of saliva taken from the user at first and second predefined times during the same day;
  providing a computer having a computer program capable of differentiating between a normal and an abnormal diurnal cortisol secretion pattern based on the first and second samples of saliva;
  storing in a database an output from an execution of said computer program; and providing a server computer, coupled to the database and adapted to present a test result associated with the output stored in the database to said user.

15. The method according to claim 14, wherein the computer program is adapted to perform, upon execution, the steps of:
  providing first and second variables;
  assigning values to the first and second variables which are associated with the cortisol concentrations in said first and second samples of saliva;
  providing a set of predefined constants for each variable;
  calculating, for each variable, a first fuzzy logic index to represent a degree to which the variable has a high value in relation to the predefined constants;
  calculating, for each variable, a second fuzzy logic index to represent a degree to which the variable has a low value in relation to the predefined constants;
  matching different combinations of the first and second fuzzy logic indices, as calculated for the first and second variables, with predetermined definitions of a normal diurnal cortisol secretion pattern and at least one abnormal diurnal cortisol secretion pattern; and
  selecting the definition where the best correspondence occurs.

16. The method according to claim 15, wherein said test result is one of the following: normal HPA axis function for said user; activated HPA axis function for said user; and blunted HPA axis function for said user.

17. The method according to claim 16, wherein said computer program in addition is capable of evaluating a level of testosterone in at least one of said first and second samples of saliva.

* * * * *

UNITED STATES PATENT AND TRADEMARK OFFICE
CERTIFICATE OF CORRECTION

PATENT NO. : 7,805,396 B2 Page 1 of 1
APPLICATION NO. : 10/448379
DATED : September 28, 2010
INVENTOR(S) : Peter Wanger et al.

It is certified that error appears in the above-identified patent and that said Letters Patent is hereby corrected as shown below:

On title page

At item (12): Please change "Wagner et al." to --Wanger et al.--.

At item (75): Please change "Peter Wagner" to --Peter Wanger--.

Signed and Sealed this

Twenty-third Day of November, 2010

David J. Kappos
*Director of the United States Patent and Trademark Office*